United States Patent
Harvey

(10) Patent No.: US 7,524,626 B2
(45) Date of Patent: Apr. 28, 2009

(54) RAPID PRODUCTION OF HIGH TITER VIRUS

(75) Inventor: Alex J. Harvey, Athens, GA (US)

(73) Assignee: Synageva BioPharma Corp., Waltham, MA (US)

( * ) Notice: Subject to any disclaimer, the term of this patent is extended or adjusted under 35 U.S.C. 154(b) by 16 days.

(21) Appl. No.: 11/542,093

(22) Filed: Oct. 3, 2006

(65) Prior Publication Data

US 2007/0077650 A1    Apr. 5, 2007

Related U.S. Application Data

(60) Provisional application No. 60/723,659, filed on Oct. 5, 2005.

(51) Int. Cl.
*C12Q 1/70* (2006.01)
*C12N 15/00* (2006.01)

(52) U.S. Cl. ......................... 435/5; 435/320.1

(58) Field of Classification Search ....................... None
See application file for complete search history.

(56) References Cited

U.S. PATENT DOCUMENTS

| 5,672,485 | A | 9/1997 | Foster et al. |
| 5,879,924 | A | 3/1999 | Foster et al. |
| 5,897,998 | A | 4/1999 | Speksnijder et al. |
| 5,985,642 | A | 11/1999 | Foster et al. |
| 6,096,534 | A | 8/2000 | Barsov et al. |
| 6,730,822 | B1 | 5/2004 | Ivarie et al. |
| 2006/0015960 | A1 | 1/2006 | Ivarie et al. |

FOREIGN PATENT DOCUMENTS

| EP | 1 548 114 A1 | 6/2005 |
| WO | WO 00/17376 | 3/2000 |

OTHER PUBLICATIONS

Watanabe and Temin. Construction of a Helper Cell Line for Avian Reticuloendotheliosis Virus Cloning Vectors. Molecular and Cellular Biology, Dec. 1983, vol. 3, No. 12; p. 2241-2249.*
Harvey, et al. Expression of exogenous protein in the egg white of transgenic chickens. Nat Biotech. 2002; 19:396-399.*
Rapp, et al. (2003) Biologically active human interferon alpha-2b produced in the egg white of transgenic hens', Transgenic Research, vol. 12, pp. 569-575.

(Continued)

*Primary Examiner*—Bruce Campell
*Assistant Examiner*—Stuart W Snyder
(74) *Attorney, Agent, or Firm*—Kyle D. Yesland

(57) ABSTRACT

The invention includes methods of producing viral particles which include introducing into avian cells a nucleotide sequence encoding a replication deficient retroviral vector and introducing into the avian cells nucleotide sequences encoding products required for replication of the replication deficient retroviral vector under the control of a promoter that is functional in the avian cell line, and harvesting the viral particles.

20 Claims, 5 Drawing Sheets

OTHER PUBLICATIONS

Bosselman et al, (1989). Science, vol. 243, p. 533-535.
Bosselman et al, (1989). Journal of Virology, p. 2680-2689.
Burns, J. C., T. Friedmann, et al, (1993). Proc Natl Acad Sci USA, 90(17):8033-7.
Chen, C. M., D. M. Smith, et al, (1999). Dev Biol, 214(2): 270-84.
Cosset et al, (1993) Virology, vol. 195, p. 385-395.
Cosset et al, (1991) J. of Virology, 65(6):3388-3394.
Cosset et al, (1992) Journal of Virology, p. 5671-5676.
Dougherty et al, (1989) Journal of Virology, p. 3209-3212.
Egrie, (1990) Pharmacotherapy Supp. vol. 10(2), p. 4S-8S.
Flamant, (1994) Int. J. Dev. Biol. 38, p. 751-757.
Harvey et al, Nature Biotechnology (2002) vol. 19, p. 396-399.
Hu et al, (1987) Virology 159(2):446-449 (Abstract).
Schaefer-Klein, J., I. Givol, et al, (1998) Virology 248(2):305-11.
Watanabe and Temin, (1982) Proc. Natl. Acad. Sci. USA, vol. 79 p. 5986-5990.

* cited by examiner

RAPID PRODUCTION OF HIGH TITER VIRUS

RELATED APPLICATION INFORMATION

This application claims the benefit of U.S. provisional application No. 60/723,659, filed Oct. 5, 2005.

BACKGROUND

This invention is directed to the production of viral particles from retroviruses which are capable of transducing cells, for example, avian cells, including germ cells. In particular, replication deficient retroviral vector particles can be produced in accordance with the invention.

Replication deficient retroviruses are particularly useful in recombinant methodologies such as gene therapy procedures and in the production of transgenic animals, for example, transgenic avians. One particularly useful transgenic animal that can be produced using replication deficient retroviruses is the transgenic chicken.

The production of an avian egg begins with formation of a large yolk in the ovary of the hen with the unfertilized ovum formed on the yolk sac. After ovulation, the yolk and ovum pass into the infundibulum of the oviduct where it is fertilized, if sperm are present, and then moves into the magnum of the oviduct which is lined with tubular gland cells. These cells secrete the egg-white proteins, including ovalbumin, ovomucoid, ovoinhibitor, conalbumin, ovomucin and lysozyme, into the lumen of the magnum where they are deposited onto the avian embryo and yolk. Researchers have been successful in producing transgenic avians in which the tubular gland cells produce the exogenous protein and secrete it into the oviduct lumen along with the egg white protein for packaging into an egg. See, for example, Harvey et al, Nature Biotechnology (2002) vol 20, p 396-399, the disclosure of which is incorporated in its entirety herein by reference and U.S. Pat. No. 6,730,822, issued May 4, 2004, the disclosure of which is incorporated in its entirety herein by reference. This system offers outstanding potential as a protein bioreactor because of the high levels of protein production, the promise of proper folding and post-translation modification of the target protein, the ease of product recovery, and the shorter developmental period of chickens compared to other animal species used for heterologous gene expression. Significantly, retroviral production in transgenic animals such as chickens can be limited by the size of the insert allowed by the retrovirus. Typically, inserts contained in the retroviruses are limited to 2 to 3 kb. Production of integration competent virus is inhibited when insert size constraints are exceeded. Important methods used to produce transgenic avians such as chickens using retroviruses involve the introduction of replication deficient yet integration competent retroviral particles into embryonic cells.

Replication deficient retroviral vectors lack certain genes required for successful reproduction of the virus. Traditionally, to produce replication deficient retroviral vectors, nucleotide sequences encoding replication deficient retroviruses have been transfected into cells which stably produce the gene products required for replication of the replication deficient retrovirus. That is, certain nucleotide sequences required for the replication of the retrovirus are missing from the retrovirus but are present in the genome of the cell in which the viral particles are produced. One system that has been used to produce replication deficient ALV retroviruses involves the use of Senta cells and Isolde cells (Cosset et al (1993) Virology vol 195, p 385-395). The process involves first transfecting nucleotide sequences encoding the replication deficient retrovirus into the Senta cells which stably produce the gag, pol and envE proteins. Viral titer obtained in the Senta cells is typically <1000/ml. To increase the titer, the viral particles produced in the Senta cells are used to transduce Isolde cells which stably produce the gag, pol and envA proteins. The retrovirus produced in this manner can contain a neomycin resistance gene which allows for selection of Isolde clones or single colonies, some of which will produce particles at high titers >10,000/ml. In spite of the production of useable amount of viral particles being produced, the titers are still relatively low using this procedure. In addition, the process is laborious and time consuming, taking typically about three months.

What is needed are new methods of producing viral particles which require less time and less labor and allow for the insertion of larger nucleotide sequences in the recipient genome and result in high titers.

SUMMARY

A retrovirus production system has been developed and is described herein in which replication deficient retroviral particles can be produced using a minimal amount of labor, can be produced in as little as 2 days, can yield titers typically ten fold or more greater than obtained by conventional methods and provides for a substantial increase in the size of nucleotide insert that can be introduced into the retroviral vector by deletion of as many as three major structural genes, i.e., gag (typically about 2000 nucleotides), pol (typically about 2300 nucleotides) and env (typically about 1500 nucleotides) protein genes. Briefly, a nucleotide sequence encoding a replication deficient retrovirus or retroviral vector is introduced into a cell such as a fibroblast cell along with nucleotide sequence that provides for replication of the replication deficient retrovirus or retroviral vector, in particular, nucleotide sequences encoding two or more of the gag, pol and env proteins are introduced into the cell. In one particularly useful embodiment, nucleotide sequences encoding all three of the gag, pol and env proteins are required for replication of the replication deficient viral vector and are introduced into the cell.

In one embodiment, methods of the invention include introducing, for example, transfecting (e.g., a transient transfection) into a cell a nucleotide sequence encoding a retroviral vector wherein the retroviral vector is replication deficient (e.g., a single nucleotide sequence containing a polynucleotide encoding a replication deficient retrovirus); introducing, for example, transfecting into the cell two or more nucleotide sequences which are under the control of promoters that are functional in the cell wherein the nucleotide sequences encode products required for replication of the replication deficient virus such as nucleotide sequences encoding gag, pol and env proteins; and harvesting viral particles.

In one particularly useful embodiment of the invention, each nucleotide sequence introduced into the cell (i.e., nucleotide sequence(s) encoding the retroviral vector and nucleotide sequence(s) encoding products required for replication of the replication deficient virus) is introduced in a transient manner. That is the nucleotide sequences are not expected to replicate in the cell and are not expected to integrate in the cellular genome. For example, the nucleotides sequences can be introduced in the cell contained in one or more bacterial plasmid vectors. The invention also contemplates, the nucleotide sequence(s) encoding products required for replication of the replication deficient virus being introduced into the cell in a transient manner and the nucleotide sequence(s) encoding the retroviral vector being introduced into the cell in a manner which provides for stable integration of the nucleotide sequence(s) into the genome of the cell. Methods are well known in the art that provide for stable integration of desired nucleotide sequences in the genome of cells, for example, cells of cell lines. For example, replication deficient retroviral vectors can be used for stable integration in a cellular genome.

The nucleotide sequence(s) encoding products required for replication of the replication deficient virus may be introduced into the cell before introduction of the nucleotide sequence(s) encoding the retroviral vector; the nucleotide sequence(s) encoding products required for replication of the replication deficient virus may be introduced into the cell at about the same time as the introduction of the nucleotide sequence(s) encoding the retroviral vector; or the nucleotide sequence(s) encoding products required for replication of the replication deficient virus may be introduced into the cell after introduction of the nucleotide sequence(s) encoding the retroviral vector.

In one embodiment, nucleotide sequences that encode products that provide for replication of the replication deficient retroviral vector are contained in one or more plasmids, for example, one plasmid for each nucleotide sequence. In certain useful embodiments, the replication deficient retroviral vector is contained in a plasmid. When nucleotide sequences are contained in a plasmid in accordance with the invention, those sequences will typically be introduced transiently into the cell.

Certain cells and cell lines that can be very useful in the present invention are avian cells (e.g., avian fibroblast cells) and avian cell lines (e.g., avian fibroblast cell lines) obtained from avians such as, chicken, turkey, duck, goose, quail, pheasants, parrots, finches, hawks, crows and ratites including ostrich, emu and cassowary. In one particularly useful embodiment, a chicken fibroblast cell line is used. However, the invention is not limited to the use of fibroblast cells and specifically contemplates any useful cell lines such as mouse cell lines, human cell lines, hamster cell lines such as CHO cells and chicken cell lines such as LMH, LMH2a cells.

In one particularly useful embodiment, the nucleotide sequence encoding a replication deficient retroviral vector encodes a retroviral vector based upon an avian retrovirus. Examples of avian retroviruses include, without limitation, Avian Leukemia/Leukosis Viruses (ALV), for example, and without limitation, RAV-0, RAV-1, RAV-2; Avian Sarcoma Viruses (ASV); Avian Sarcoma/Acute Leukemia Viruses (ASLV) including, without limitation, Rous Sarcoma Virus (RSV); Fujinami Sarcoma Viruses (FSV); Avian Myeloblastosis Viruses (AMV); Avian Erythroblastosis Viruses (AEV); Avian Myelocytomatosis Viruses (MCV), for example, and without limitation, MC29; Reticuloendotheliosis Viruses (REV), for example, and without limitation, Spleen Necrosis Virus (SNV). The invention also contemplates that the nucleotide sequence encoding a replication deficient retroviral vector can encode any useful retroviral vector, including, without limitation, retroviral vectors based upon Murine Leukemia Viruses (MLV); Molony Murine Sarcoma Viruses (MMSV); Moloney Murine Leukemia Viruses (MMLV); and lentiviruses (e.g., human immunodeficiency virus (HIV), feline immunodeficiency virus (FIV), bovine immunodeficiency virus (BIV) and simian immunodeficiency virus (SIV).

In one particularly useful embodiment, the nucleotide sequence(s) that encodes the products required for replication of the replication deficient virus is nucleotide sequence obtained or derived from the genome of an avian retrovirus. Examples of avian retroviruses contemplated for such use include, without limitation, Avian Leukemia/Leukosis Viruses (ALV), for example, and without limitation, RAV-0, RAV-1, RAV-2; Avian Sarcoma Viruses (ASV); Avian Sarcoma/Acute Leukemia Viruses (ASLV) including, without limitation, Rous Sarcoma Virus (RSV); Fujinami Sarcoma Viruses (FSV); Avian Myeloblastosis Viruses (AMV); Avian Erythroblastosis Viruses (AEV); Avian Myelocytomatosis Viruses (MCV), for example, and without limitation, MC29; Reticuloendotheliosis Viruses (REV), for example, and without limitation, Spleen Necrosis Virus (SNV). The invention also contemplates the nucleotide sequence encoding a product required for replication of the replication deficient virus being nucleotide sequence obtained or derived from the genome of any useful retrovirus, including, without limitation, Murine Leukemia Viruses (MLV); Molony Murine Sarcoma Viruses (MMSV); Moloney Murine Leukemia Viruses (MMLV); and lentiviruses (e.g., human immunodeficiency virus (HIV), feline immunodeficiency virus (FIV), bovine immunodeficiency virus (BIV) and simian immunodeficiency virus (SIV).

Included in one specific aspect of the invention are methods of producing a viral particle which comprise introducing (e.g., transfecting) into a fibroblast cell line nucleotide sequences required for replication of the replication defective retroviral vector, for example, nucleotide sequences encoding gag, pol and env proteins wherein the gag, pol and env protein coding sequences are under the control of a promoter that is functional in the fibroblast cell line; introducing (e.g., transfecting) into the fibroblast cell line a nucleotide sequence encoding a replication deficient retroviral vector; and harvesting the viral particles.

In one embodiment, the gag, pol and env protein coding sequences required for replication of the replication defective retroviral vector are contained in one or more plasmids. For example, the gag, pol and env protein coding sequences may all be contained in one plasmid or each may be contained in a separate plasmid. In another example, two of the gag, pol and env protein coding sequences (e.g., gag and pol) may be present on one plasmid and the third may be present on another plasmid (e.g., the env).

In one aspect, the nucleotide sequence encoding the retroviral vector is a provirus. That is, the nucleotide sequence encoding the retroviral vector is DNA that has been integrated into a host cell genome. In one embodiment, the nucleotide sequence encoding the retroviral vector is present in a plasmid.

In one particularly useful embodiment, the gag, pol and env protein encoding nucleotide sequences are from an avian retrovirus. Examples of avian retroviruses include, without limitation, Avian Leukemia/Leukosis Viruses (ALV), for example, and without limitation, RAV-0, RAV-1, RAV-2; Avian Sarcoma Viruses (ASV); Avian Sarcoma/Acute Leukemia Viruses (ASLV) including, without limitation, Rous Sarcoma Virus (RSV); Fujinami Sarcoma Viruses (FSV); Avian Myeloblastosis Viruses (AMV); Avian Erythroblastosis Viruses (AEV); Avian Myelocytomatosis Viruses (MCV), for example, and without limitation, MC29; Reticuloendotheliosis Viruses (REV), for example, and without limitation, Spleen Necrosis Virus (SNV). It is also contemplated that the gag, pol and env protein encoding nucleotide sequences required for replication of the replication defective retroviral vector can be derived or obtained from any useful retroviral vector, including, without limitation, retroviral vectors based upon Murine Leukemia Viruses (MLV); Molony Murine Sarcoma Viruses (MMSV); Moloney Murine Leukemia Viruses (MMLV); and lentiviruses (e.g., human immunodeficiency virus (HIV), feline immunodeficiency virus (FIV), bovine immunodeficiency virus (BIV) and simian immunodeficiency virus (SIV).

In certain embodiments, the nucleotide sequences required for replication of the replication defective retroviral vector may not all be from the same virus. For example, a gag protein may be from the Avian Leukosis Virus (ALV), a pol protein may be from the Molony Murine Sarcoma Virus (MMSV), and an env protein may be from the Avian Erythroblastosis Viruses (AEV). In another example, a gag protein may be from the Molony Murine Sarcoma Virus (MMSV) an env protein may be from the Avian Leukosis Virus (ALV). These are only examples provided for illustrative purposes and the invention is not limited thereto.

Though specific embodiments of the invention require three nucleotide sequences for replication of the replication defective retroviral vector, for example, sequences encoding the gag, pol and env proteins, the invention is not limited thereto. For example, only one or two nucleotide sequence may be required to provide products necessary for replication of the replication defective retroviral vector.

In one aspect, the invention is directed to methods of producing transgenic avians. The methods typically include harvesting viral particles produced as disclosed herein and introducing the harvested retroviral particles into avian embryo cells such as early stage embryos, for example, stage I to stage XII embryos, and thereafter obtaining a hatched chick derived from the embryo cells.

Certain references which may be relevant to the present invention, the disclosures of which are incorporated herein in their entirety by reference, include: Burns, J. C., T. Friedmann, et al. (1993). "Vesicular stomatitis virus G glycoprotein pseudotyped retroviral vectors: concentration to very high titer and efficient gene transfer into mammalian and nonmammalian cell" Proc Natl Acad Sci USA 90(17): 8033-7; Chen, C. M., D. M. Smith, et al. (1999). "Production and design of more effective avian replication-incompetent retroviral vectors." Dev Biol 214(2): 370-84; Cosset et al (1991) "Improvements of Avian Leukosis Virus (ALV)-Based Retrovirus Vectors by Using Different cis-Acting Sequences from ALVs" J. of Virology 65(6): 3388-3394; Schaefer-Klein, J., I. Givol, et al. (1998). "The EV-O-derived cell line DF-1 supports the efficient replication of avian leukosis-sarcoma viruses and vectors."Virology 248(2): 305-11; U.S. Pat. No. 6,096,534, issued Aug. 1, 2000; U.S. Pat. No. 5,672,485, issued Sep. 30, 1997; U.S. Pat. No. 5,985,642, issued Nov. 16, 1999; and U.S. Pat. No. 5,879,924, issued Mar. 9, 1999.

Any combination of features described herein is included within the scope of the present invention provided that the features included in any such combination are not mutually inconsistent. Such combinations will be apparent based on this specification and upon the knowledge of one of ordinary skill in the art.

DETAILED DESCRIPTION

Figure 1:
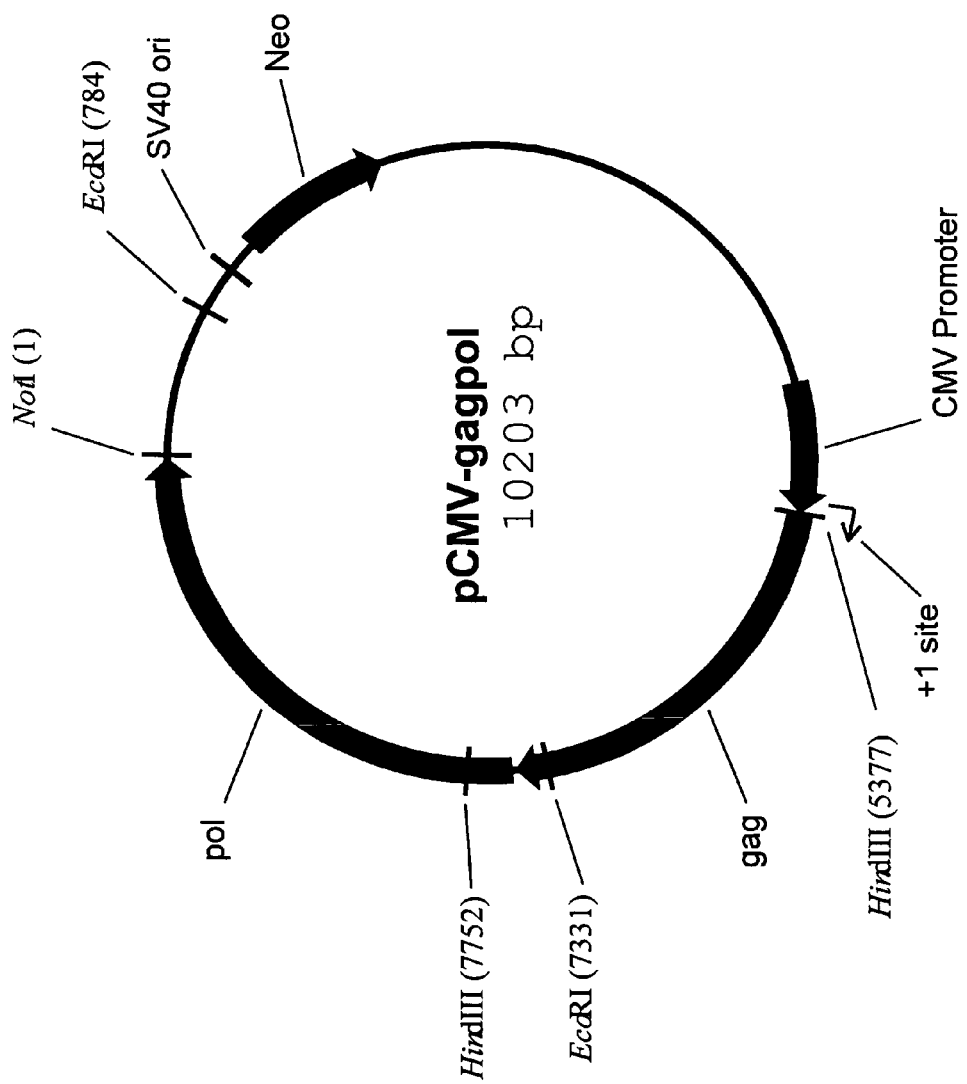
FIG. 1 shows a map of pCMV-gagpol which contains coding sequences for the RSV gag protein and the RSV pol protein.

Certain definitions are set forth herein to illustrate and define the meaning and scope of the various terms used to describe the invention herein.

The term "avian" as used herein refers to any species, subspecies *or* strain of organism of the taxonomic class ava, such as, but not limited to chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Australorp, Minorca, Amrox, California Gray), as well as strains of turkeys, pheasants, quails, duck, ostriches and other poultry commonly bred in commercial quantities. It also includes an individual avian organism in all stages of development, including embryonic and fetal stages. The term "avian" also may denote "pertaining to a bird", such as "an avian (bird) cell."

A "nucleic acid or polynucleotide sequence or nucleotide sequence" includes, but is not limited to, mRNA, cDNA, genomic DNA, and synthetic DNA and RNA sequences, comprising the natural nucleoside bases adenine, guanine, cytosine, thymidine, and uracil. The term also encompasses sequences having one or more modified bases such as, without limitation, pseudo uridine, 2-amino purine, deoxy uridine and deoxyinosine.

"Therapeutic proteins" or "pharmaceutical proteins" include an amino acid sequence which in whole or in part makes up a drug.

"Transgene" is a DNA sequence inserted into a genome, i.e., an exogenous DNA sequence. A transgene may refer to the entire sequence that is inserted, for example, the inserted retrovirus plus any sequences carried by the retrovirus. "Transgene" may also refer to the sequence of interest carried by the retrovirus, for example, a coding sequence and promoter or, for example, the nucleotide sequence between the LTRs of the inserted retrovirus.

The phrase "based on" or "based upon" as in a retroviral vector being based on a particular retrovirus or based on a nucleotide sequence of a particular retrovirus mean that the genome of the retroviral vector contains a substantial portion of the nucleotide sequence of the genome of the particular retrovirus. The substantial portion may be a particular gene or nucleotide sequence such as the nucleotide sequence encoding the gag, pol and/or env proteins or other structural or functional nucleotide sequence of the virus genome such as sequences encoding the LTRs or may be substantially the complete retrovirus genome, for example, most (e.g., more than 60% or more than 70% or more than 80% or more than 90%) or all of the retrovirus genome, as will be apparent from the context in the specification as the knowledge of one skilled in the art. Examples of retroviral vectors that are based on a retrovirus are the NL retroviral vectors (e.g., NLB) which are based on the ALV retrovirus as disclosed in Cosset et al, Journal of Virology (1991) vol 65, p 3388-3394. NL vectors such as NLB, NLD and NLA are contemplated for use in methods of the present invention.

A "coding sequence" or "open reading frame" refers to a nucleotide sequence which can be transcribed and translated (in the case of DNA) or translated (in the case of mRNA) into a polypeptide in vitro or in vivo when placed under the control of appropriate regulatory sequences. The boundaries of the coding sequence are determined by a translation start codon at the 5' (amino) terminus and a translation stop codon at the 3' (carboxy) terminus. A transcription termination sequence will usually be located 3' to the coding sequence. A coding sequence may be flanked on the 5' and/or 3' ends by untranslated regions.

Nucleic acid "controlling sequences" or "regulatory sequences" refer to promoter sequences, translational start and stop codons, ribosome binding sites, polyadenylation signals, transcription termination sequences, upstream regulatory domains, enhancers, and the like, as necessary and sufficient for the transcription and translation of a given coding sequence in a defined host cell. Examples of control sequences suitable for eukaryotic cells are promoters, polyadenylation signals, and enhancers. All of these control sequences need not be present in a recombinant vector so long as those necessary and sufficient for the transcription and translation of the desired gene are present.

"Operably or operatively linked" refers to the configuration of the coding and control sequences so as to perform the desired function. Thus, control sequences operably linked to a coding sequence are capable of effecting the expression of the coding sequence. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "heterologous" and "exogenous" as they relate to nucleic acid sequences such as coding sequences and control sequences, denote sequences that are not normally associated with a region of a recombinant construct or with a particular chromosomal locus, and/or are not normally associated with a particular cell. Thus, an "exogenous" region of a nucleic acid construct is an identifiable segment of nucleic acid within or attached to another nucleic acid molecule that is not found in association with the other molecule in nature. For example, an exogenous region of a construct could include a coding sequence flanked by sequences not found in association with the coding sequence in nature. Another example of an exogenous coding sequence is a construct where the coding sequence itself is not found in nature (e.g., synthetic sequences having codons different from the native gene). Similarly, a host cell transformed with a construct or nucleic acid which is not normally present in the host cell would be considered exogenous for purposes of this invention.

"Exogenous protein" or "heterologous protein" as used herein refers to a protein not naturally present in a particular tissue or cell, a protein that is the expression product of an exogenous expression construct or transgene, or a protein not naturally present in a given quantity in a particular tissue or cell. A protein that is exogenous to an egg is a protein that is not normally found in the egg. For example, a protein exogenous to an egg may be a protein that is present in the egg as a result of the expression of a coding sequence present in a transgene of the animal laying the egg.

The expression products described herein may consist of proteinaceous material having a defined chemical structure. However, the precise structure depends on a number of factors, particularly chemical modifications common to proteins. For example, since all proteins contain ionizable amino and carboxyl groups, the protein may be obtained in acidic or basic salt form, or in neutral form. The primary amino acid sequence may be derivatized using sugar molecules (glycosylation) or by other chemical derivatizations involving covalent or ionic attachment with, for example, lipids, phosphate, acetyl groups and the like, often occurring through association with saccharides. These modifications may occur in vitro, or in vivo, the latter being performed by a host cell through posttranslational processing systems. Such modifications may increase or decrease the biological activity of the molecule, and such chemically modified molecules are also intended to come within the scope of the invention.

"Vector" means a polynucleotide comprised of single strand, double strand, circular, or supercoiled DNA or RNA. A typical vector may include the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements may be omitted in specific applications. The nucleic acid cassette can include one or more restriction sites for insertion of the nucleic acid sequence to be expressed. In a functional vector the nucleic acid cassette contains the nucleic acid sequence to be expressed including translation initiation and termination sites. An intron optionally may be included in the construct, for example, 5' to the coding sequence. A vector is constructed so that the particular coding sequence is located in the vector with the appropriate regulatory sequences, the positioning and orientation of the coding sequence with respect to the control sequences being such that the coding sequence is transcribed under the "control" of the controlling or regulatory sequences. Modification of the sequences encoding the particular protein of interest may be desirable to achieve this end. For example, in some cases it may be necessary to modify the sequence so that it may be attached to the control sequences with the appropriate orientation; or to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

A "retroviral vector" is a retrovirus or a modified retrovirus or virus that can be used to shuttle nucleotide sequences into a cell. The term virus, viral vector, retrovirus and retroviral vector may be used interchangeably throughout the specification.

A "promoter" is a site on the DNA to which RNA polymerase binds to initiate transcription of a gene. In some embodiments the promoter will be modified by the addition or deletion of sequences, or replaced with alternative sequences, including natural and synthetic sequences as well as sequences which may be a combination of synthetic and natural sequences. Many eukaryotic promoters contain two types of recognition sequences: the TATA box and the upstream promoter elements. The former, located upstream of the transcription initiation site, is involved in directing RNA polymerase to initiate transcription at the correct site, while the latter appears to determine the rate of transcription and is upstream of the TATA box. Enhancer elements can also stimulate transcription from linked promoters, but many function exclusively in a particular cell type. Many enhancer/promoter elements derived from viruses, e.g., the SV40 promoter, the cytomegalovirus (CMV) promoter, the rous-sarcoma virus (RSV) promoter, and the murine leukemia virus (MLV) promoter are all active in a wide array of cell types, and are termed "constitutive" or "ubiquitous". An example of a non-constitutive promoter is the mouse mammary tumor virus (MMTV) promoter. The nucleic acid sequence inserted in the cloning site may have any open reading frame encoding a polypeptide of interest, with the proviso that where the coding sequence encodes a polypeptide of interest, it should lack cryptic splice sites which can block production of appropriate mRNA molecules and/or produce aberrantly spliced or abnormal mRNA molecules.

A "marker gene" is a gene which encodes a protein that allows for identification and isolation of correctly transfected cells. Suitable marker sequences include, but are not limited to green, yellow, and blue fluorescent protein genes (GFP, YFP, and BFP, respectively). Other suitable markers include thymidine kinase (tk), dihydrofolate reductase (DHFR), and aminoglycoside phosphotransferase (APH) genes. The latter imparts resistance to the aminoglycoside antibiotics, such as kanamycin, neomycin, and geneticin. These, and other marker genes such as those encoding chloramphenicol acetyltransferase (CAT), β-lactamase, β-galactosidase (β-gal), may be incorporated into the primary nucleic acid cassette along with the gene expressing the desired protein, or the selection markers may be contained in separate vectors and cotransfected.

The term "plasmid" as used herein typically refers to a vector that cannot reproduce in a eukaryotic cell and typically does not integrate into the genome of a eukaryotic cell. Plasmids are particularly useful in producing transient transfection.

A "reporter gene" is a marker gene that "reports" its activity in a cell by the presence of the protein that it encodes.

A "replication deficient" virus or viral vector is a virus or viral vector that is missing an element from its genome that is required for replication.

A "retroviral particle", "transducing particle", or "transduction particle" refers to a replication-defective or replication-competent virus or retrovirus capable of transducing non-viral DNA or RNA into a cell.

The terms "transformation", "transduction" and "transfection" all denote the introduction of a polynucleotide into a cell.

"Magnum" is that part of the oviduct between the infundibulum and the isthmus containing tubular gland cells that synthesize and secrete the egg white proteins of the egg.

The term "optimized" is used in the context of "optimized coding sequence", wherein the most frequently used codons for each particular amino acid found in the egg white proteins ovalbumin, lysozyme, ovomucoid, and ovotransferrin are used in the design of optimized polynucleotide sequence, encoding exogenous protein, that can be inserted into retroviral vectors or particles produced according to the present invention. More specifically, the optimized DNA sequence is based on the hen oviduct optimized codon usage and may be produced using the BACKTRANSLATE program of the Wisconsin Package, Version 9.1 (Genetics Computer Group Inc., Madison, Wis.) with a codon usage table compiled from the chicken (*Gallus gallus*) ovalbumin, lysozyme, ovomucoid, and ovotransferrin proteins. For example, the percent usage for the four codons of the amino acid alanine in the four egg white proteins is 34% for GCU, 31% for GCC, 26% for GCA, and 8% for GCG. Therefore, GCU is used as the codon for the majority of alanines in the optimized human IFN-α 2b coding sequence, the amino acid sequence of which is well known in the art. The vectors containing the gene for optimized human IFN-α 2b are used to create transgenic avians that express transgenic poultry derived IFN-α 2b (TPD IFN-α 2b) in their tissues and eggs. Similarly, the above method is employed for the design of the optimized human erythropoietin (EPO) polynucleotide sequence in order to create transgenic avians that express transgenic poultry derived erythropoietin (TPD EPO) in their tissues and eggs.

The invention is directed to producing viral particles capable of transduction of cells, for example, avian cells, including embryonic cells. In particular, replication deficient retroviral vectors can be produced in accordance with the invention.

The invention contemplates the application of any useful cell to be employed in accordance with the present invention, such as avian cells. In one particularly useful embodiment, the cells used herein are immortal; that is, the cells are capable of continuous growth in culture.

Fibroblast cells (i.e., fibroblast cell lines) have shown to be particularly useful as disclosed herein, though the invention is not limited thereto. For example, the invention contemplates the use of human fibroblast cells, rabbit fibroblast cells, bovine fibroblast cells, reptile fibroblast cells, fibroblast cells from fishes or other useful fibroblast cells. In one particularly useful aspect of the invention, avian fibroblast cells are employed. The invention is not limited to the use of any particular avian fibroblast cells; however, examples of avians from which fibroblast cells may be derived for use in accordance with the invention include, without limitation, turkeys, ducks, geese, quail, pheasants, parrots, finches, hawks, crows and ratites including ostrich, emu and cassowary. One particularly useful type of avian fibroblast cell for use as disclosed herein is the chicken fibroblast cell. Fibroblast cells of any variety of chicken (i.e., *Gallus gallus*), such as, but not limited to, White Leghorn, Brown Leghorn, Barred-Rock, Sussex, New Hampshire, Rhode Island, Australorp, Minorca, Amrox and California Gray can be used.

Fibroblast cells typically are cells present in or cells that give rise to connective tissue. In one aspect, fibroblast cells are cells that give rise to collagen. Fibroblast cells may be defined as cells that secrete an extracellular matrix rich in collagen. Fibroblast cells may be derived from a variety of sources. For example, the invention contemplates fibroblast cells obtained from tissue such as muscle tissue and from organs such as the liver, skin and lungs. In one embodiment, the invention contemplates the use of embryo fibroblast cells such as chicken embryo fibroblast cells, for example, immortal chicken embryo fibroblast cell lines. A particularly useful fibroblast cell line (DF-1) is disclosed in U.S. Pat. No. 5,672,485, issued Sep. 30, 1997, the disclosure of which is incorporated in its entirety herein by reference.

The invention contemplates the introduction of certain nucleotide sequences into cells; i.e., nucleotide sequences encoding replication deficient retroviruses and nucleotide sequences that encode products required for replication of the replication deficient retrovirus, for example, two or more of gag, pol and env proteins. The products required are typically biomolecules that are necessary for replication or propagation of the retrovirus. For example, and without limitation, proteins required for replication or propagation of the retrovirus can be: viral polymerase; one or more proteins contained in the viral envelope; one or more proteins contained in the capsid.

The nucleotide sequences introduced into the cells may be in any useful form. For example, the nucleotide sequences may be DNA or RNA. The nucleotide sequences introduced into the cells may be in linear form or circular form. In one embodiment, the nucleotide sequences are contained in a circular vector.

Any useful vector may be employed in the present invention. Typically, vectors of the invention are not designed to integrate into the genome of cells used for there production and are also designed not to replicate inside of the cell. Many commercially available vectors such as plasmids or phagemids are available that can be used in accordance with the invention, such as pBluescript®, pBR322, pUC19, pDRIVE and others.

In one embodiment, the nucleotide sequences are transiently introduced into the cell by any useful method. For example, the nucleotide sequences may be introduced into the cells using, for example, electroporation, calcium phosphate precipitation, microinjection, sonication, microparticle bombardment as well as using dendrimers, PEI, polylysine and polyamine and other techniques, each as is understood by a practitioner of skill in the art. One particularly useful method of introducing the nucleotide sequences into the cells is by transfection, for example, lipofection. Methods of transfecting cells by lipofection are well known in the art. Examples of lipofection reagents that can be used in accordance with the invention include, without limitation, DMRIE C, FuGENE and Lipofectamine™.

By the methods of the present invention, transgenes contained in viral particles produced in accordance with the present invention, can be introduced into avian embryonic blastodermal cells, to produce a transgenic chicken, transgenic turkey, transgenic quail and other avian species, that carries the transgene in the genetic material of its germ-line tissue. The blastodermal cells may be stage I to XII cells, or the equivalent thereof, and are typically near stage X (e.g., stage VII to stage XII). Retroviral particles produced as disclosed herein are also contemplated for use in transducing primordial germ cells from later stage embryos, including embryos from stage 13 to stage 30. Typically, though not exclusively, the blastodermal cells are present inside of a hard shell egg. The cells useful for producing transgenic avians include cells termed embryonic germ (EG) cells, embryonic stem (ES) cells & primordial germ cells (PGCs). It is contemplated that the embryonic blastodermal cells may be isolated freshly, maintained in culture, or, in a particularly useful embodiment, reside in situ within an embryo.

Examples of viral particles which can be produced in accordance with the invention include replication deficient viral particles that contain a coding sequence for a useful protein which is linked to a promoter that provides for expression of the useful protein in a host cell, for example, a cell of a transgenic animal. For example, the useful protein can be a human protein or other useful protein such as those disclosed herein. In one embodiment, the viral particles may be used to produce exogenous proteins in specific tissues of an avian, for example, in the oviduct tissue of an avian. In a particularly useful embodiment, the viral particles are used in methods to produce avians that lay eggs which contain exogenous protein.

In one particular embodiment of the invention, an avian retroviral vector such as an ALV based vector such as NLB is cotransfected into a fibroblast cell line (e.g., a chicken fibroblast cell line) such as DF-1 cells (e.g., via lipofection) along with a rous sarcoma virus (RSV) gag-pol expression vector and a third vector which expresses an envelope protein, for example, an envelope protein of the vesicular stomatitis virus (VSV-G) or of ALV (envA). After 48 hours, the media is harvested and contains high titer ALV based retroviral particles. The virus particles can be concentrated by centrifugation to achieve even higher titers. In a certain embodiment, the cells are treated with sodium butyrate which provides for a further increase in viral titer.

In one embodiment, in the genome of the viral particles produced as disclosed herein, the exogenous protein coding sequence and the promoter are both positioned between 5' and 3' LTRs. The vector may include a marker nucleotide sequence, wherein the marker nucleotide sequence is operably linked to a promoter.

In one embodiment, the viral vectors produced in accordance with the invention include a signal peptide coding sequence which is operably linked to the exogenous protein coding sequence, so that upon translation in a cell, the signal peptide will direct secretion of the exogenous protein expressed by the vector into the egg white and the exogenous protein will be packaged into a hard shell egg.

In certain embodiments, introduction of a vector of the present invention into the embryonic blastodermal cells is performed with embryonic blastodermal cells that are either freshly isolated or in culture. The transgenic cells are then typically injected into the subgerminal cavity beneath a recipient blastoderm in an egg. In some cases, however, the vector is delivered directly into the subgerminal cavity of a blastodermal embryo in situ.

In one embodiment of the invention, viral particles used for transfecting blastodermal cells and generating stable integration in the avian genome contain a coding sequence and a promoter in operational and positional relationship to express the coding sequence in the tubular gland cell of the magnum of the avian oviduct, wherein the coding sequence codes for an exogenous protein which is deposited in the egg white of a hard shell egg. The promoter may be a portion of a promoter that is particularly active (i.e., highly expressed) in tubular gland cells such as the ovalbumin promoter, ovomucoid promoter or lysozyme promoter. Therefore, in one embodiment, the promoter is a non-constitutive promoter. The invention contemplates truncating such promoters and/or condensing the critical regulatory elements of the promoters so that it retains sequences required for expression in the tubular gland cells of the magnum of the oviduct, while being small enough that it can be readily incorporated into genome of the viral particles. The invention also contemplates the use of a fusion promoter. In another particularly useful embodiment, the promoter is a constitutive promoter, for example, and without limitation, a cytomegalovirus (CMV) promoter, a rous-sarcoma virus (RSV) promoter, a murine leukemia virus (MLV) promoter or a beta-actin promoter or a LTR promoter.

Therefore, in one embodiment of the invention, the promoter is a cytomegalovirus (CMV) promoter, a rous-sarcoma virus (RSV) promoter, a murine leukemia virus (MLV) promoter, a beta-actin promoter, a mouse mammary tumor virus (MMTV) promoter, a LTR promoter, an ovalbumin promoter, a lysozyme promoter, a conalbumin promoter, an ovomucoid promoter, an ovomucin promoter, and an ovotransferrin promoter or combinations thereof. In one embodiment, the promoter contains a segment of a promoter region, such as a segment of the ovalbumin-, lysozyme-, conalbumin-, ovomucoid-, ovomucin-, and ovotransferrin promoter. In a particularly useful embodiment, the promoter contains at least a portion of the CMV promoter.

If desired, transducing particles (i.e., transduction particles) produced in accordance with the invention can be titered by any useful method as is understood by a practitioner of skill in the art. For example, if the viral genome contains a marker such as a neomycin resistance gene, the particles can be titered by transduction of cells and serial dilution followed by plating and counting of colonies. In one embodiment, the titer is determined by hybridization to the vial genome (e.g., quantitative densitometry of a probed blot of the viral nucleic acid (RNA or DNA) as is understood by practitioners of skill in the art). Immunofluorescence or ELISA analysis to quantitate viral coat protein and quantitative PCR of the viral genome, for example, quantitative PCR of the reverse transcription product from the viral genome can also be used.

In one embodiment, viral particles of the invention are introduced into avian blastodermal cells by egg windowing methods, for example, in accordance with the Speksnijder procedure (U.S. Pat. No. 5,897,998). That is, the viral particles are introduced into the blastodermal cells in situ, for example, by introduction into the subgerminal cavity of the embryo. After introduction (e.g., injection), the eggs hatch after about 21 days. Typically, male birds are selected for breeding. In order to screen for G0 roosters which contain the transgene (e.g., introduced nucleotide sequence) in their sperm, DNA is extracted from rooster sperm samples. The G0 roosters with the highest levels of the transgene in their sperm samples can be bred to nontransgenic hens by artificial insemination. Blood DNA samples are screened for the presence of the transgene and in the case of avians produced for exogenous protein production, the blood may be assayed (e.g., ELISA) for the exogenous protein. If presence of the exogenous protein is confirmed, the sperm of the G1 transgenic roosters can be used for artificial insemination of nontransgenic hens. A certain percent of the G2 offspring will contain the transgene (e.g., about 50%).

Transgenic avians produced from the blastodermal cells are known as founders. Some founders will carry the transgene in the tubular gland cells in the magnum of their oviducts. These avians can express the exogenous protein encoded by the transgene in their oviducts. The exogenous protein may also be present in other tissues (e.g., blood) in addition to the oviduct. If the exogenous protein contains the appropriate signal sequence(s), it may be secreted into the lumen of the oviduct and into the egg white of the egg. Some founders are germ-line founders. A germ-line founder is a founder that carries the transgene in genetic material of its germ-line tissue, and may or may not carry the transgene in tubular gland cells which express the exogenous protein. Therefore, in accordance with the invention, the transgenic avian may have tubular gland cells expressing the exogenous protein. Regardless if the founder contains the genetic material in its tubular gland cells, if the founder is a germ-line founder some of its offspring will be completely transgenic (i.e., not chimeric) and will have tubular gland cells that express the exogenous protein. In certain embodiments, the offspring can express a phenotype determined by expression of the exogenous gene in only specific tissue(s) of the avian, for example, by use of a tissue specific promoter.

In one specific example, for the production of transgenic chickens as disclosed herein, a CMV promoter was linked to the coding sequence of erythropoietin (165 amino acid form; see, for example, Pharmacotherapy (1990) Supplement to vol 10, No. 2, p 3S to 8S, the disclosure of which is incorporated in its entirety herein by reference) to form a cassette which was inserted into an ALV vector. The retroviral vector was produced transiently and concentrated to approximately $1 \times 10^7$ particles/ml. 3 to 7 ul of concentrated virus was injected in the subgerminal cavity of windowed Charles River SPF line 21 unincubated eggs. Chicks were hatched and raised to sexual maturity. Males were screened for the presence of the transgene in their sperm DNA by quantitative PCR for the gene of interest, in this case EPO.

In one embodiment, the retroviral particles produced as disclosed herein are used to produce transgenic avians used to express, in large yields and at low cost, a wide range of desired proteins including those used as human and animal pharmaceuticals, diagnostics, and livestock feed additives. For example, the invention includes transgenic avians that produce such proteins and eggs laid by the transgenic avians which contain the protein, for example, in the egg white. The present invention is contemplated for use in the production of any desired protein including pharmaceutical proteins with the requisite that the coding sequence of the protein can be introduced into an oviduct cell in accordance with the present invention. In one particularly useful embodiment, the proteins produced as disclosed herein are human proteins, i.e., proteins produced by humans.

The invention, therefore, includes methods for producing multimeric proteins including immunoglobulins, such as antibodies, and antigen binding fragments thereof. Thus, in one embodiment of the present invention, the multimeric protein is an immunoglobulin, wherein the first and second heterologous polypeptides are immunoglobulin heavy and light chains respectively In certain embodiments, an immunoglobulin polypeptide encoded by the transcriptional unit of at least one expression vector may be an immunoglobulin heavy chain polypeptide comprising a variable region or a variant thereof, and may further comprise a D region, a J region, a C region, or a combination thereof. An immunoglobulin polypeptide produced as disclosed herein may also be an immunoglobulin light chain polypeptide comprising a variable region or a variant thereof, and may further comprise a J region and a C region. The present invention also contemplates multiple immunoglobulin regions that are derived from the same animal species, or a mixture of species including, but not only, human, mouse, rat, rabbit and chicken. In certain embodiments, the antibodies are human or humanized.

In other embodiments, the immunoglobulin polypeptide produced as disclosed herein comprises an immunoglobulin heavy chain variable region, an immunoglobulin light chain variable region, and a linker peptide thereby forming a single-chain antibody capable of selectively binding an antigen.

Examples of therapeutic antibodies that may be produced in methods of the invention include but are not limited to HERCEPTIN™ (Trastuzumab) (Genentech, CA) which is a humanized anti-HER2 monoclonal antibody for the treatment of patients with metastatic breast cancer; REOPRO™ (abciximab) (Centocor) which is an anti-glycoprotein IIb/IIIa receptor on the platelets for the prevention of clot formation; ZENAPAXT™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope); IgG antibody (ImClone System); IMC-C225 which is a chimeric anti-EGFR IgG antibody; VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD2O IgG1 antibody (IDEC Pharm/Genentech, Roche/Zettyaku); LYMPHOCIDE™ which is a humanized anti-CD22 IgG antibody (Immunomedics); ICM3 which is a humanized anti-ICAM3 antibody (ICOS Pharm); IDEC-114 which is a primate anti-CD80 antibody (IDEC Pharm/Mitsubishi); ZEVALIN™ which is a radiolabelled murine anti- CD20 antibody (IDEC/Schering AG); IDEC-131 which is a humanized anti-CD40L antibody (IDEC/Eisai); IDEC-151 which is a primatized anti-CD4 antibody (IDEC); IDEC-152 which is a primatized anti-CD23 antibody (IDEC/Seikagaku); SMART anti-CD3 which is a humanized anti-CD3 IgG (Protein Design Lab); 5G1.1 which is a humanized anti-complement factor 5 (CS) antibody (Alexion Pharm); D2E7 which is a humanized anti-TNF-α antibody (CAT/BASF); CDP870 which is a humanized anti-TNF-α Fab fragment (Celltech); IDEC-151 which is a primatized anti-CD4 IgG1 antibody (IDEC Pharm/SmithKline Beecham); MDX-CD4 which is a human anti-CD4 IgG antibody (Medarex/Eisai/Genmab); CDP571 which is a humanized anti-TNF-α IgG4 antibody (Celltech); LDP-02 which is a humanized anti-α4μ7 antibody (Leukosite/Genentech); OrthoClone OKT4A which is a humanized anti-CD4 IgG antibody (Ortho Biotech); ANTOVA™ which is a humanized anti-CD40L IgG antibody (Biogen); ANTEGREN™ which is a humanized anti-VLA-4 IgG antibody (Elan); and CAT-152 which is a human anti-TGF-μ$_2$ antibody (Cambridge Ab Tech).

Other specific examples of therapeutic proteins which are contemplated for production as disclosed herein include, without limitation, factor VIII, b-domain deleted factor VIII, factor viia, factor ix, anticoagulants, hirudin, alteplase, tpa, reteplase, tpa, tpa-3 of 5 domains deleted, insulin, insulin lispro, insulin aspart, insulin glargine, long-acting insulin analogs, hgh, glucagons, tsh, follitropin-beta, fsh, gm-csf, pdgh, ifn alpa2a, inf-apha, inf-beta 1b, ifn-beta 1a, ifn-gamma1b, il-2, il-11, hbsag, ospa, murine mab directed against t-lymphocyte antigen, murine mab directed against tag-72, tumor-associated glycoprotein, fab fragments derived from chimeric mab, murine mab fragment directed against tumor-associated antigen ca125, murine mab fragment directed against human carcinoembryonic antigen, cea, murine mab fragment directed against human cardiac myosin, murine mab fragment directed against tumor surface antigen psma, murine mab fragments (fab/fab2 mix) directed against hmw-maa, murine mab fragment (fab) directed against carcinoma-associated antigen, mab fragments (fab) directed against nca 90, a surface granulocyte nonspecific cross reacting antigen, chimeric mab directed against cd20 antigen found on surface of b lymphocytes, humanized mab directed against the alpha chain of the il2 receptor, chimeric mab directed against the alpha chain of the il2 receptor, chimeric mab directed against tnf-alpha, humanized mab directed against an epitope on the surface of respiratory synctial virus, humanized mab directed against her 2, i.e., human epidermal growth factor receptor 2, human mab directed against cytokeratin tumor-associated antigen anti-ctla4, chimeric mab directed against cd 20 surface antigen of b lymphocytes domase-alpha dnase, beta glucocerebrosidase, tnf-alpha, il-2-diptheria toxin fusion protein, tnfr-lgg fragment fusion protein laronidase, dnaases, alefacept, darbepoetin alfa (colony stimulating factor), tositumomab, murine mab, alemtuzumab, rasburicase, agalsidase beta, teriparatide, parathyroid hormone derivatives, adalimumab (lgg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker and lbritumomab tiuxetan.

The invention specifically provides for the production of useful human proteins such as human proteins which have application as pharmaceutical proteins. For example, the invention provides for the production of human cytokines (such as human interferon (IFN), human erythropoietin (EPO), human growth hormone, human G-CSF, human GM-CSF), human antibodies and other useful human proteins. Other proteins which are desirably expressed as disclosed herein include lysozyme, β-casein, albumin, α-1 antitrypsin, antithrombin III, collagen, factors VIII, IX, X, and the like, fibrinogen, hyaluronic acid, insulin, lactoferrin, protein C, tissue-type plasminogen activator (tPA), feed additive enzymes, somatotropin, and chymotrypsin. Genetically engineered antibodies, such as immunotoxins which bind to surface antigens on human tumor cells and destroy them, can also be expressed for use as pharmaceuticals or diagnostics.

The following specific examples are intended to illustrate the invention and should not be construed as limiting the scope of the claims.

EXAMPLE 1

Vector Construction

Construction of pCMV-gagpol pRC/CMV (Invitrogen, Inc.) was digested with Not I and Hind III and the linearized 5376 bp vector was gel purified. The gag region of the Rous Sarcoma Virus (RSV) was amplified from RSV using Pfu polymerase and the following primers: RSV-gag-1-2, GGCAAGCTTGGATCAAGCATG-GAAGCCGTCATAAAGGT (SEQ ID NO:1) and RSV-gag-2, TGGGAATTCCTCCTCCTATGC (SEQ ID NO:2). The RSV PCR product was digested with EcoRI and Hind III and the 1954 bp fragment containing the gag region was gel purified. The pol region of the Rous Sarcoma Virus (RSV) was amplified with Elongase enzyme mix (Invitrogen, Inc.) using the following primers: RSV-pol1, ACACTGGGAGT-CACCCGGTCAAACAG (SEQ ID NO:3) and RSV-pol2, GGGTCGACGCGGCCGCTTAACTCTCGT-TGGCAGCAAG (SEQ ID NO:4). The PCR product was digested with EcoRI and NotI and a 2873 bp fragment containing the pol region was gel purified.

The linearized pRC/CMV, the RSV gag PCR product and the RSV pol PCR product were ligated together to produce the 10,203 bp pCMV-gagpol vector (FIG. 1).

Construction of pNLB-CMV-EPO pNLB-CMV-hIFN alpha-2b (see U.S. Pat. No. 6,730,822, issued May 4, 2004 and U.S. patent application Ser. No. 11/167,052, filed Jun. 24, 2005, the disclosures of which are incorporated in their entirety herein by reference) was digested with Hind III and EcoRI in order to replace the hIFN coding sequence of interest plus signal peptide coding sequence with an EPO coding sequence plus signal peptide (SEQ ID NO:11). Because multiple EcoRI and Hind III sites exist in the vector, RecA-assisted restriction endonuclease (RARE) cleavage method was used to cut the desired sites. The following oligonucleotides were used in the RARE procedure:

pnlbEcoRI3805rare(5'-GAC TCC TGG AGC CCG TCA GTA TCG GCG GAA TTC CAG CTG AGC GCC GGT CGC TAC CAT TAC-3') (SEQ ID NO:5) and pnlbHinD III3172rare (5'-TAA TAC GAC TCA CTA TAG GGA GAC CGG AAG CTT TCA CCA TGG CTT TGA CCT TTG CCT TAC-3') (SEQ ID NO:6).

A linearized vector of 8740 bp was obtained and was gel purified.

The EPO insert was prepared by overlap PCR as follows.

Figure 2:
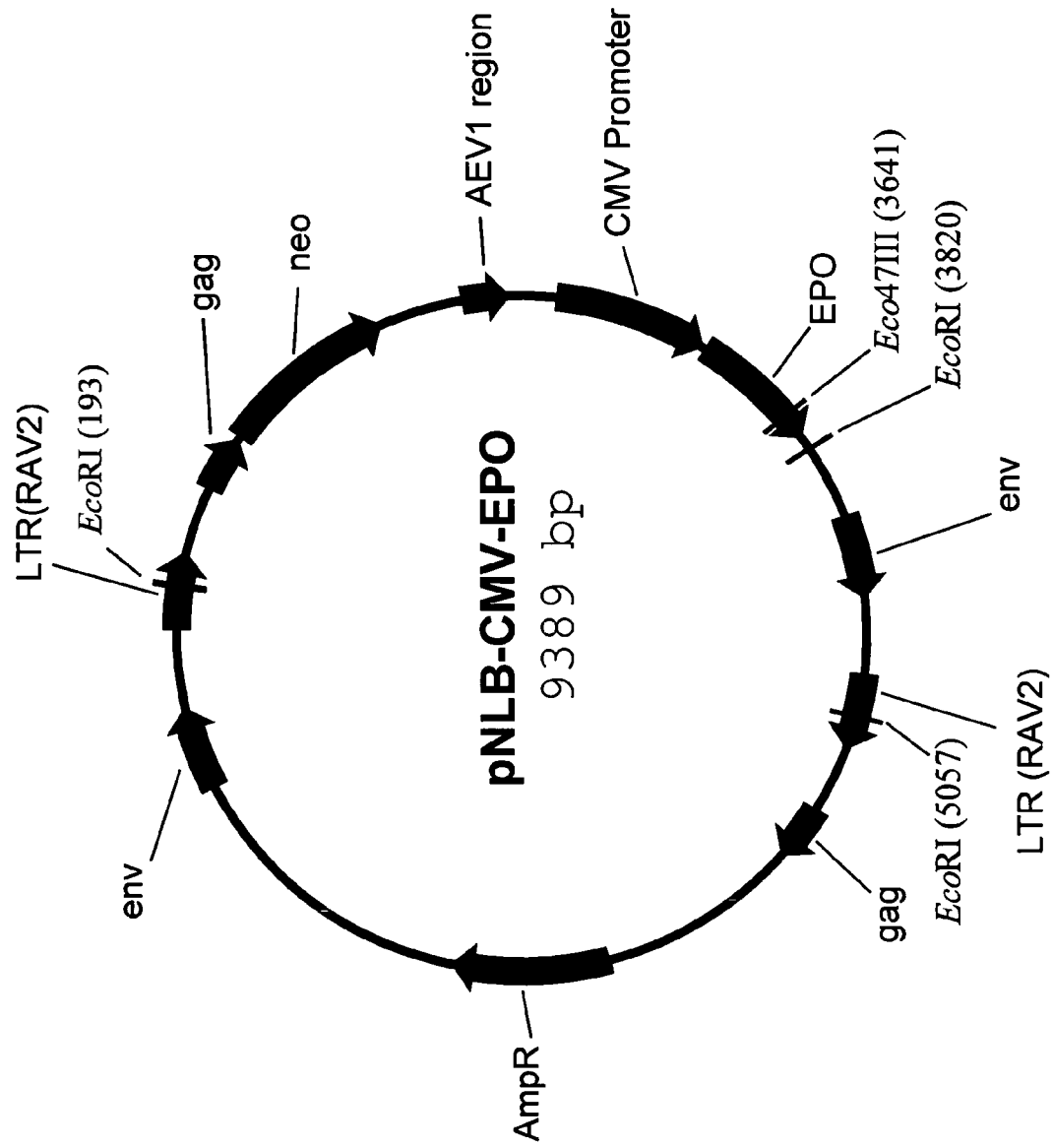
FIG. 2 shows a map of pNLB-CMV-EPO which contains the replication deficient pNLB vector coding sequence containing an expression cassette comprising a CMV promoter and an erythropoietin coding sequence (EPO 166 amino acids).

The first PCR product was produced by amplification of a synthetic EPO sequence (EPO 1) cloned into a standard cloning vector with Pfu polymerase and the following primers:

5'pNLB/Epo (5'-GGGGGGAAGCTTTCACCATGGGCGT-GCACGAG-3') (SEQ ID NO:7) and pNLB/3'Epo (5'-TC-CCCATACTAGACTTTTTACCTATCGCCGGTC-3') (SEQ ID NO:8). The 2$^{nd}$ PCR product was produced by amplification of a region of pNLB-CMV-hIFN alpha-2b with Pfu polymerase and the following primers: 3'Epo/pNLB (5'-ACCG-GCGATAGGTAAAAAGTCTAGTATGGG-3') (SEQ ID NO:9) and pNLB/SapI (5'-GGGGGGGCTCTTCT-CAGCTGGAATTCCGCCGATAC-3') (SEQ ID NO:10). The two PCR products were mixed and reamplified with the following primers: 5'pNLB/Epo (5'-GGGGG-GAAGCTTTCACCATGGGCGTGCACGAG-3') (SEQ ID NO:7) and pNLB/SapI (5'-GGGGGGGCTCTTCT-CAGCTGGAATTCCGCCGATAC-3') (SEQ ID NO:10). The fusion PCR product was digested with Hind III and Eco RI and a 633 bp fragment gel purified. The 8740 bp and 633 bp fragments were ligated to create pNLB-CMV-EPO (FIG. 2).

```
                                         (SEQ ID NO:11)
EPO 1 - Synthetic EPO sequence (610 nt)

AAGCTTTCACCATGGGCGTGCACGAGTGCCCTGCTTGGCTGTGGCTGCTC

TTGAGCCTGCTCAGCCTGCCTCTGGGCCTGCCTGTGCTGGGCGCTCCTCC

AAGGCTGATCTGCGATAGCAGGGTGCTGGAGAGGTACCTGCTGGAGGCTA

AGGAGGCTGAGAACATCACCACCGGCTGCGCTGAGCACTGCAGCCTGAAC

GAGAACATCACCGTGCCTGATACCAAGGTGAACTTTTACGCTTGGAAGAG

GATGGAGGTGGGCCAGCAGGCTGTGGAGGTGTGGCAGGGCCTGGCTCTGC

TGAGCGAGGCTGTGCTGAGGGGCCAGGCTCTGCTGGTGAACAGCTCTCAG

CCTTGGGAGCCTCTGCAGCTGCACGTGGATAAGGCTGTGAGCGGCCTGAG

AAGCCTGACCACCCTGCTGAGGGCTCTGAGGGCTCAGAAGGAGGCTATCA

GCCCTCCAGATGCTGCAAGCGCTGCCCCTCTGAGGACCATCACCGCTGAT

ACCTTTAGGAAGCTGTTTAGGGTGTACAGCAACTTTCTGAGGGGCAAGCT

GAAGCTGTACACCGGCGAGGCTTGCAGGACCGGCGATAGGTAAAAAGGCC

GGCCGAGCTC
```

Construction of pNLB-CMV-Des-Arg166-EPO

Figure 3:
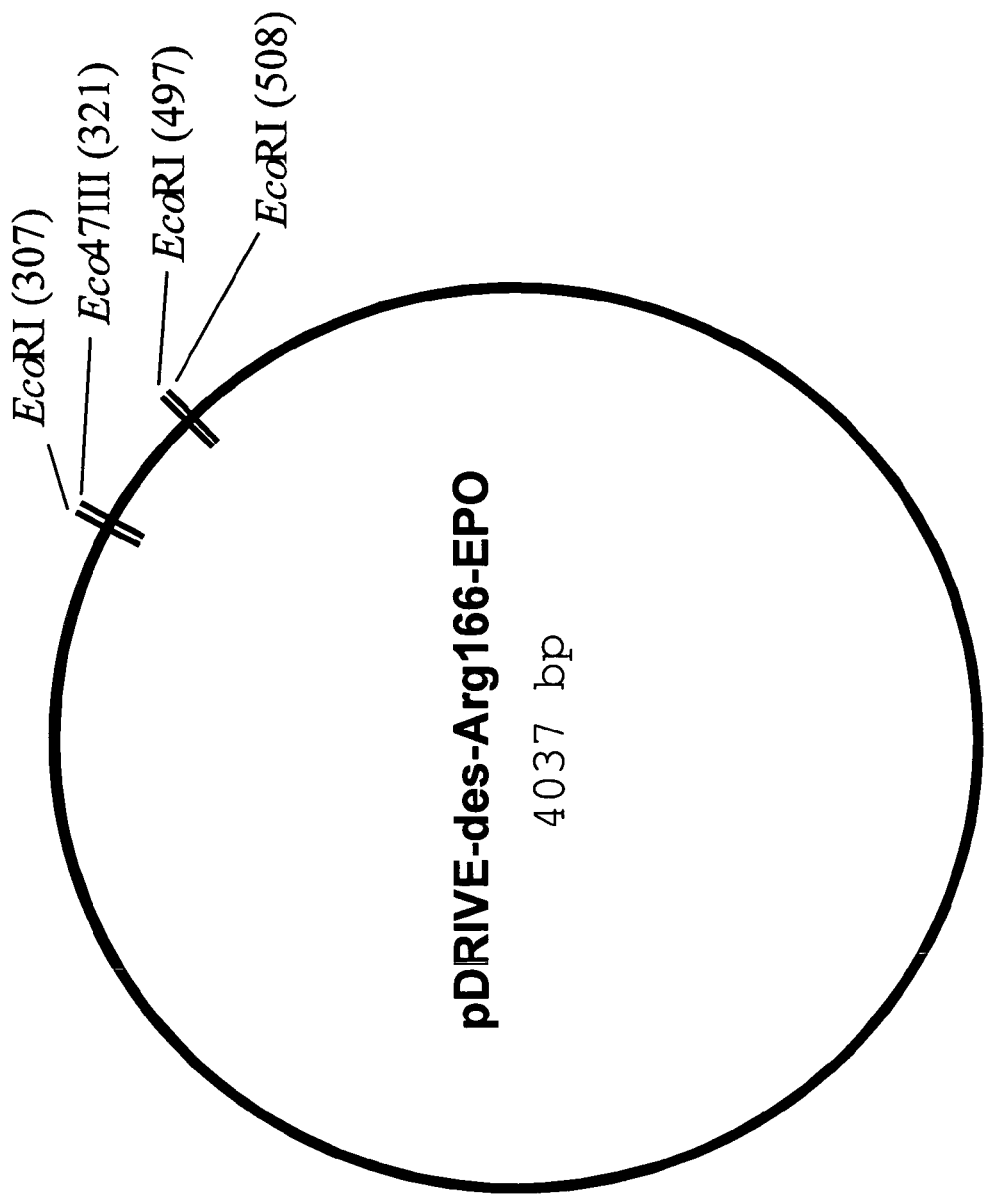
FIG. 3 shows a pDRIVE vector containing a nucleotide sequence useful for altering the erythropoietin coding sequence in the pNLB-CMV-EPO vector to the 165 amino acid encoding form.
Figure 4:
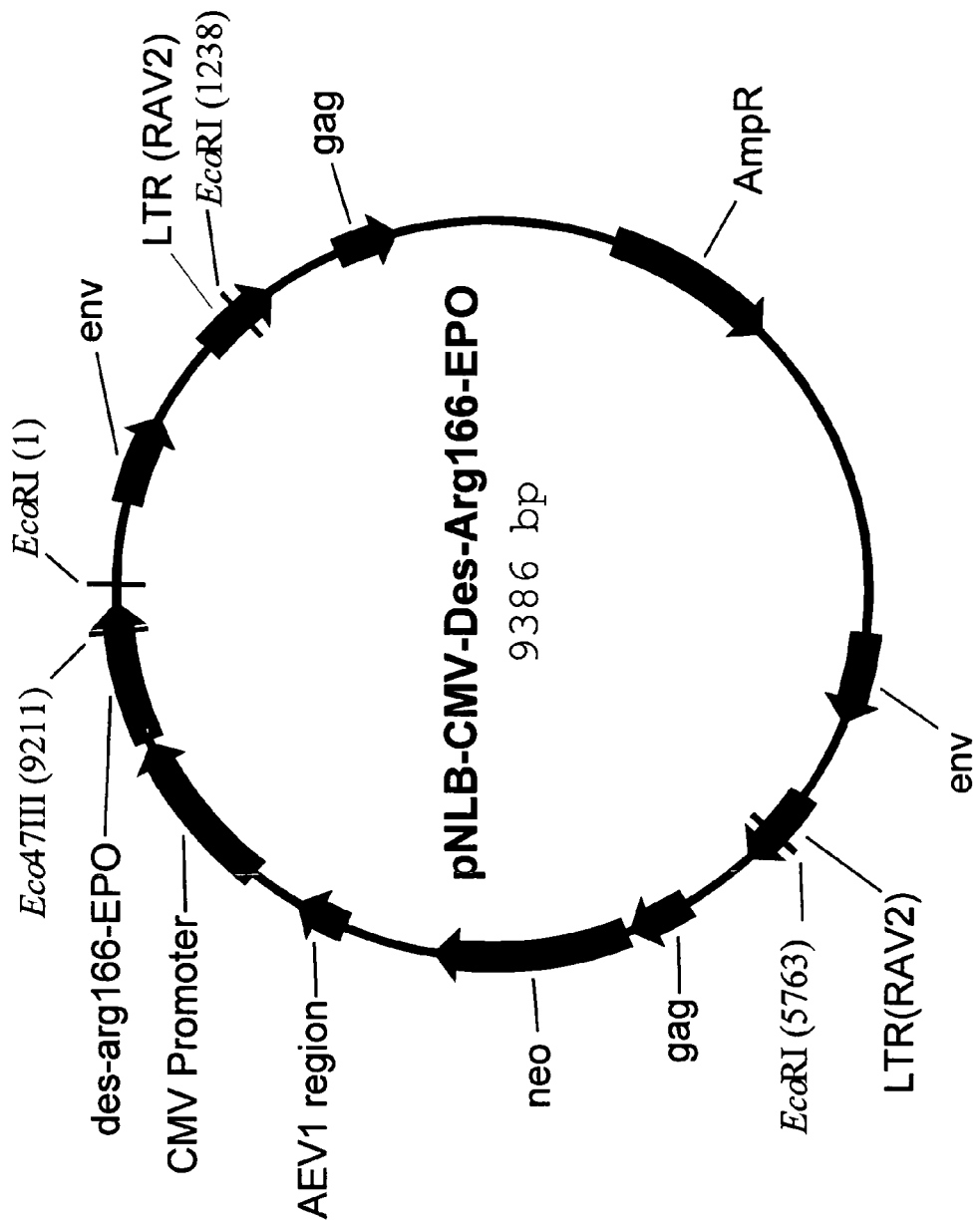
FIG. 4 shows a map of pDRIVE-des-Arg166-EPO which contains the coding sequence for the 165 amino acid form of human erythropoietin (terminal arginine removed).
Figure 5:
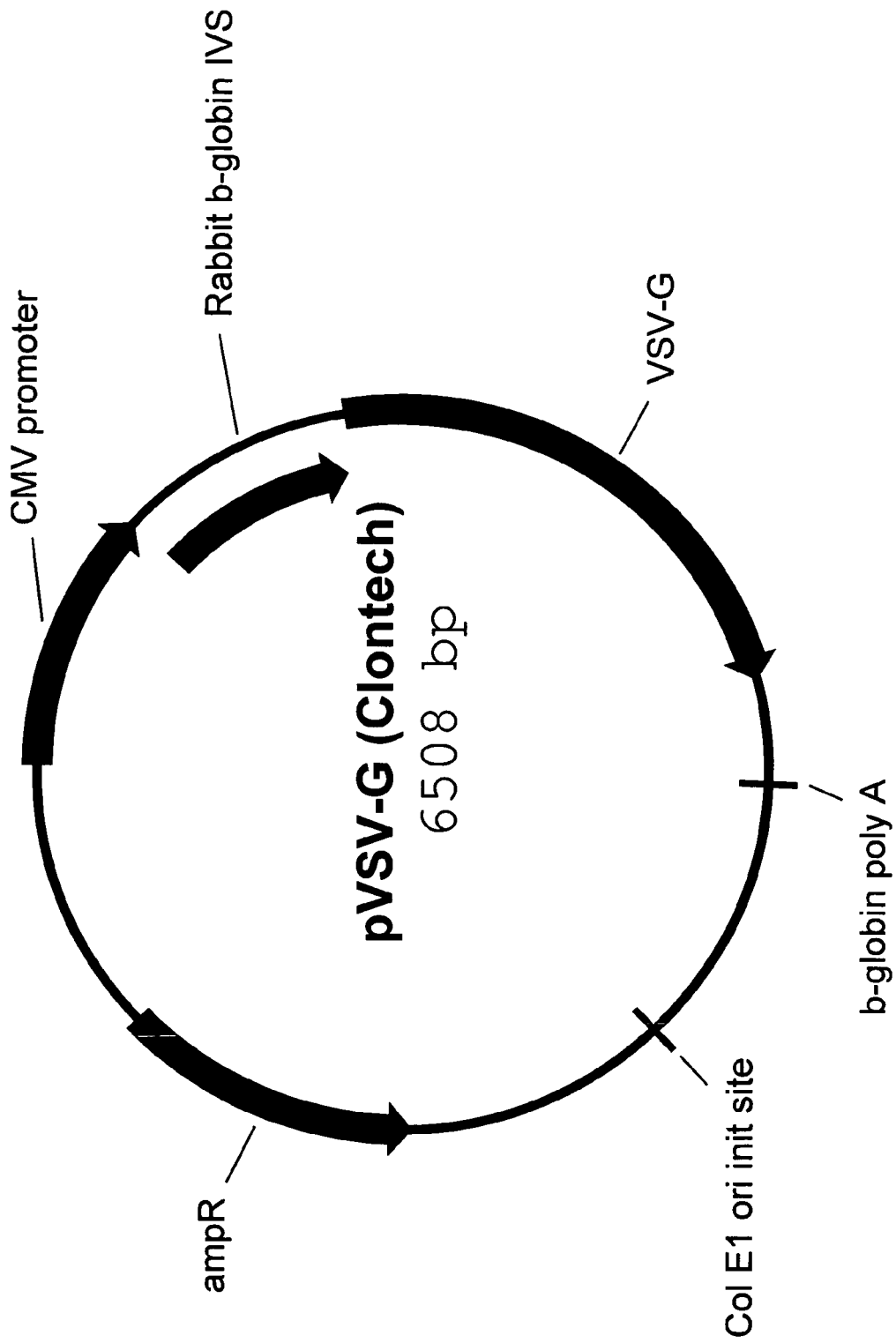
FIG. 5 shows commercially available pVSV-G.

An EPO coding sequence is produced which codes for a 165 amino acid form of EPO with the terminal codon (coding for arginine at position 166) removed. A 179 bp region of pNLB-CMV-EPO corresponding to the sequence that extends from an Eco 47III site that resides in the EPO coding sequence to an EcoRI site that resides downstream of the EPO stop codon in pNLB-CMV-EPO was synthesized with the terminal arginine codon (position 166) eliminated so that aspartic acid (amino acid 165) will be the terminal amino acid codon, resulting in a 176 bp Eco 47III/EcoRI fragment. The fragment was synthesized by Integrated DNA Technologies (Coralville, Iowa 52241) and cloned into a pDRIVE vector (Qiagen, Inc), creating pDRIVE-des-Arg166-EPO (FIG. 3). The 176 bp Eco 47III/EcoRI fragment was subcloned into the Eco47III/EcoRI site of pNLB-CMV-EPO, creating pNLB-CMV-Des-Arg166-EPO (FIG. 4).

EXAMPLE 2

Transient Transfection of DF-1 Cells

The day before transfection, 3.7×10$^6$ DF-1 cells were plated in 150 mm tissue culture dishes in DF-1 media (Dulbecco's Modified Eagle Medium with high glucose, L-glutamine, pyridoxine HCl, 10% fetal bovine serum, 10 U/ml penicillin G and 10 ug/ml streptomycin) and cultured at 37° C. with 6% CO2. The next day the cells were transfected as follows. Each plate was washed with 6 ml OptiMEM (Invitrogen, Inc.) and refed with 5 ml OptiMEM. 18.4 ug of the retrovector, pNLB-CMV-Des-Arg166-EPO, 18.4 ug of pCMV-gagpol and 0.92 ug of pVSV-G were mixed in 4.6 ml OptiMEM in a 15 ml polystyrene tube or bottle. 110 ul of DMRIE-C was mixed with 4.6 ml OptiMEM. The lipid/OptiMEM was added to the DNA/optiMEM. After mixing by inverting or swirling, the transfection mix was incubated at RT for 15 minutes and then added to one 150 mm plate. The plate was incubated at 37° C. with 6% CO2 for 3 to 4 hours. The transfection mix was removed, the plate was washed once with 6 ml DF-1 media and refed with 20 ml DF-1 media. In certain instances sodium butyrate may be added at this stage (for example, about 2 mM to about 40 mM) and the cells incubated overnight. In such case, the medium is removed the next morning and the cells are again washed with DF-1 media. Such treatment with sodium butyrate can increase the viral particle titer about 5 to 10 fold over the titer that would otherwise be obtained without use of sodium butyrate. The plate was incubated at 37° C. with 6% CO2 for 18 to 60 hours and the media from the plate harvested by pouring into and filtering through a Millipore SteriCup Vacuum Filter, 0.45 um PVDF 250 ml (cat no. SCHV U02 RE).

Filtered viral media from two transfected 150 mm plates was poured into Beckman SW28 Ultraclear tubes (cat no. 344058). The media was centrifuged in a SW28 rotor at 19.4 krpm, for 2 hours at 4° C. Most of the super was removed and DF-1 media filtered with a 0.2 uM filter was added to a final volume of 100 to 400 ul. The viral pellet was resuspended at 4° C. for 1 to 4 hrs or overnight. The media and pellet were further resuspended by triturating with a Gilman P200 pipettor 3-4 times and the viral resuspension was transferred to a Nunc Cryo vial and frozen at −70° C. To titer, aliquots of the viral resuspension were thawed in 37° C. water bath, diluted with DF-1 media and plated on Senta or DF-1 cells. One to two days later, media containing G418 at 200 ug/ml was added to the Senta or DF-1 cells. Media was changed every two to three days and colonies were counted when evident. Titer of concentrated virus was approximately 1×10$^7$ (without sodium butyrate treatment) which is approximately a 10 fold higher titer than typically obtained using traditional methods to produce replication deficient retroviral particles, such as the methods disclosed in U.S. Pat. No. 6,730,822, issued May 4, 2004, the disclosure of which is incorporated in its entirety by reference, which discloses the use of Senta and Isolde cells for the production of NLB replication deficient retroviral vectors.

EXAMPLE 3

Production of Transgenic Birds 7 ul of the virus suspension prepared according to Example 2 was injected into the subgerminal cavity of 97 fertile, unincubated White Leghorn eggs (Charles River, SPAFAS). 54 chicks hatched and were reared to sexual maturity. Semen was collected and DNA extracted by the Chelex method. 100 ng of sperm DNA, as determined by the PicoGreen assay (Molecular Probes) was assayed for the presence of the EPO transgene using the Applied Biosystems TaqMan® Fast Universal PCR Master Mix and the Applied Biosystems 7900HT. The primers were: SJ-EPO-for, 5'-GCCCTCCAGATGCTG-CAA-3' (SEQ ID NO:12) and SJ-EPO-rev, 5'-CCCTAAA-CAGCTTCCTAAAGGTATCA-3' (SEQ ID NO:13). The Taqman EPO probe sequence was 5'-CGCTGCCCCTCT-GAGGACCATC-3' (SEQ ID NO:14) and was labeled with FAM (6-carboxyfluorescin) at the 5' end and TAMRA (N,N,N',N'-tetramethyl-6-carboxyrhodamine) at the 3'end. One rooster was found to have a significant level of the EPO gene in his semen. This rooster was bred to wildtype hens. Approximately 144 chicks were hatched. Their blood DNA was extracted and tested for the presence of the transgene using the EPO Taqman assay. Two chicks were found to be positive for the transgene. The quantity of the transgene was such that every cell would be calculated to have one copy of the EPO transgene, as would be expected for a G1.

All documents (e.g., U.S. patents, U.S. patent applications, publications) cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method comprising:
   transiently introducing into a cell a nucleotide sequence encoding an avian retroviral vector wherein the avian retroviral vector is replication deficient;
   transiently introducing into the cell nucleotide sequence encoding products required for replication of the replication deficient retroviral vector, the products being gag, pol and env proteins; and
   harvesting viral particles.

2. The method of claim 1 wherein the nucleotide sequence encoding products required for replication of the replication deficient retroviral vector is contained in one or more plasmids.

3. The method of claim 1 wherein the nucleotide sequence encoding an avian retroviral vector is DNA.

4. The method of claim 1 wherein the replication deficient retroviral vector is contained in a plasmid.

5. The method of claim 1 wherein each introducing is facilitated by transfection.

6. The method of claim 1 wherein the cell is an avian cell.

7. The method of claim 1 wherein the cell is a chicken cell.

8. The method of claim 1 wherein the cell is a fibroblast cell.

9. The method of claim 1 wherein the nucleotide sequence encoding a retroviral vector encodes a retroviral vector based on a retrovirus selected from the group consisting of Avian Leukemia/Leukosis Viruses (ALV), RAV-0, RAV-1, RAV-2, Avian Sarcoma Viruses (ASV), Avian Sarcoma/Acute Leukemia Viruses (ASLV), Rous Sarcoma Virus (RSV), Fujinami Sarcoma Viruses (FSV), Avian Myeloblastosis Viruses (AMV), Avian Erythroblastosis Viruses (AEV), Avian Myelocytomatosis Viruses (MCV), MC29, Reticuloendotheliosis Viruses (REV) and Spleen Necrosis Virus (SNV).

10. The method of claim 1 wherein the nucleotide sequence encoding a retroviral vector encodes a retroviral vector based on Avian Leukemia/Leukosis Viruses (ALV).

11. The method of claim 1 wherein the nucleotide sequence encoding products required for replication of the replication deficient retroviral vector is nucleotide sequence from a retrovirus selected from the group consisting of Avian Leukemia/Leukosis Viruses (ALV), RAV-0, RAV-1, RAV-2, Avian Sarcoma Viruses (ASV), Avian Sarcoma/Acute Leukemia Viruses (ASLV), Rous Sarcoma Virus (RSV), Fujinami Sarcoma Viruses (FSV), Avian Myeloblastosis Viruses (AMV), Avian Erythroblastosis Viruses (AEV), Avian Myelocytomatosis Viruses (MCV), MC29, Reticuloendotheliosis Viruses (REV) and Spleen Necrosis Virus (SNV), or combinations thereof.

12. The method of claim 1 wherein the retrovirus contains a coding sequence for an exogenous protein operably linked to a promoter.

13. The method of claim 12 wherein the exogenous protein is a therapeutic protein.

14. The method of claim 12 wherein the exogenous protein is a human protein.

15. A method comprising:
   transiently introducing into an avian cell line a nucleotide sequence encoding an avian retroviral vector wherein the avian retroviral vector is replication deficient;
   transiently introducing into the avian cell line one or more nucleotide sequences wherein the nucleotide sequence(s) encode products required for replication of the replication deficient retroviral vector the products being gag, pol and env proteins; and
   harvesting viral particles.

16. The method of claim 15 wherein the nucleotide sequence encoding an avian retroviral vector is DNA.

17. The method of claim 15 wherein each introducing is facilitated by transfection.

18. The method of claim 15 wherein the avian cell line is a chicken fibroblast cell line.

19. The method of claim 15 wherein the nucleotide sequence encoding a retroviral vector is based on a retrovirus selected from the group consisting of Avian Leukemia/Leukosis Viruses (ALV), RAV-0, RAV-1, RAV-2, Avian Sarcoma Viruses (ASV), Avian Sarcoma/Acute Leukemia Viruses (ASLV), Rous Sarcoma Virus (RSV), Fujinami Sarcoma Viruses (FSV), Avian Myeloblastosis Viruses (AMV), Avian Erythroblastosis Viruses (AEV), Avian Myelocytomatosis Viruses (MCV), MC29, Reticuloendotheliosis Viruses (REV) and Spleen Necrosis Virus (SNV).

20. A method comprising:
   introducing into a cell a nucleotide sequence encoding an avian retroviral vector wherein the avian retroviral vector is replication deficient;
   introducing into the cell nucleotide sequence wherein the nucleotide sequence encodes products required for replication of the replication deficient retroviral vector, the products being the gag, pol and env proteins;
   harvesting viral particles;
   introducing the harvested particles into avian blastodermal cells; and
   obtaining a transgenic avian species.

* * * * *

SEQUENCE LISTING

<160> NUMBER OF SEQ ID NOS: 14

<210> SEQ ID NO 1
<211> LENGTH: 38
<212> TYPE: DNA
<213> ORGANISM: Rous sarcoma virus

<400> SEQUENCE: 1
ggcaagcttg gatcaagcat ggaagccgtc ataaaggt                    38

<210> SEQ ID NO 2
<211> LENGTH: 21
<212> TYPE: DNA
<213> ORGANISM: Rous sarcoma virus

<400> SEQUENCE: 2
tgggaattcc tcctcctatg c                                      21

<210> SEQ ID NO 3
<211> LENGTH: 26
<212> TYPE: DNA
<213> ORGANISM: Rous sarcoma virus

<400> SEQUENCE: 3
acactgggag tcacccggtc aaacag                                 26

<210> SEQ ID NO 4
<211> LENGTH: 37
<212> TYPE: DNA
<213> ORGANISM: Rous sarcoma virus

<400> SEQUENCE: 4
gggtcgacgc ggccgcttaa ctctcgttgg cagcaag                     37

<210> SEQ ID NO 5
<211> LENGTH: 60
<212> TYPE: DNA
<213> ORGANISM: Avian leukosis virus

<400> SEQUENCE: 5
gactcctgga gcccgtcagt atcggcggaa ttccagctga gcgccggtcg ctaccattac    60

<210> SEQ ID NO 6
<211> LENGTH: 60
<212> TYPE: DNA
<213> ORGANISM: Avian leukosis virus

<400> SEQUENCE: 6
taatacgact cactataggg agaccggaag ctttcaccat ggctttgacc tttgccttac    60

```
<210> SEQ ID NO 7
<211> LENGTH: 32
<212> TYPE: DNA
<213> ORGANISM: Homo sapiens

<400> SEQUENCE: 7 gggggggaagc tttcaccatg ggcgtgcacg ag                                    32

<210> SEQ ID NO 8
<211> LENGTH: 33
<212> TYPE: DNA
<213> ORGANISM: Homo sapiens

<400> SEQUENCE: 8
tccccatact agactttta cctatcgccg gtc                                     33

<210> SEQ ID NO 9
<211> LENGTH: 30
<212> TYPE: DNA
<213> ORGANISM: Homo sapiens

<400> SEQUENCE: 9
accggcgata ggtaaaaagt ctagtatggg                                        30

<210> SEQ ID NO 10
<211> LENGTH: 35
<212> TYPE: DNA
<213> ORGANISM: Avian leukosis virus

<400> SEQUENCE: 10 ggggggggctc ttctcagctg gaattccgcc gatac                                 35

<210> SEQ ID NO 11
<211> LENGTH: 610
<212> TYPE: DNA
<213> ORGANISM: Homo sapiens

<400> SEQUENCE: 11
aagctttcac catgggcgtg cacgagtgcc ctgcttggct gtggctgctc ttgagcctgc       60
tcagcctgcc tctgggcctg cctgtgctgg gcgctcctcc aaggctgatc tgcgatagca     120
gggtgctgga gaggtacctg ctggaggcta aggaggctga aacatcacc accggctgcg      180
ctgagcactg cagcctgaac gagaacatca ccgtgcctga taccaaggtg aacttttacg      240
cttggaagag gatggaggtg ggccagcagg ctgtggaggt gtggcagggc ctggctctgc     300
tgagcgaggc tgtgctgagg ggccaggctc tgctggtgaa cagctctcag ccttgggagc     360
ctctgcagct gcacgtggat aaggctgtga cggcctgag aagcctgacc accctgctga      420
gggctctgag ggctcagaag gaggctatca gccctccaga tgctgcaagc gctgccctc      480
tgaggaccat caccgctgat acctttagga agctgttag ggtgtacagc aacttttctga     540
ggggcaagct gaagctgtac accggcgagg cttgcaggac cggcgatagg taaaaaaggcc     600
ggccgagctc                                                            610

<210> SEQ ID NO 12
<211> LENGTH: 18
<212> TYPE: DNA
<213> ORGANISM: Homo sapiens

<400> SEQUENCE: 12
gccctccaga tgctgcaa                                                     18
```

```
<210> SEQ ID NO 13
<211> LENGTH: 26
<212> TYPE: DNA
<213> ORGANISM: Homo sapiens

<400> SEQUENCE: 13
ccctaaacag cttcctaaag gtatca                                          26

<210> SEQ ID NO 14
<211> LENGTH: 22
<212> TYPE: DNA
<213> ORGANISM: Homo sapiens

<400> SEQUENCE: 14 cgctgccct ctgaggacca tc                                               22
```